United States Patent [19]
Palmer et al.

[11] Patent Number: 6,068,607
[45] Date of Patent: May 30, 2000

[54] COLD COMPRESS FOR HUMAN GENITALIA

[76] Inventors: William Timothy Palmer; Shannon H. Palmer, both of 3176 Whitemarsh Cir., Farmers Branch, Tex. 75234

[21] Appl. No.: 09/276,133

[22] Filed: Mar. 25, 1999

[51] Int. Cl.7 ....................................................... A61F 13/00
[52] U.S. Cl. ................................. 602/67; 602/70; 607/112
[58] Field of Search ................................ 602/67, 68, 69, 602/70, 72, 73; 128/845, 842; 607/112–114

[56] References Cited

U.S. PATENT DOCUMENTS

| | | |
|---|---|---|
| 3,506,013 | 4/1970 | Zdenek . |
| 3,782,375 | 1/1974 | Donars . |
| 4,092,982 | 6/1978 | Salem . |
| 4,253,464 | 3/1981 | Zorgniotti et al. . |
| 4,534,354 | 8/1985 | Bonner, Jr. et al. . |
| 4,556,055 | 12/1985 | Bonner, Jr. et al. . |
| 4,596,250 | 6/1986 | Beisang, III . |
| 4,679,554 | 7/1987 | Markham . |
| 5,003,972 | 4/1991 | Kestler . |
| 5,716,319 | 2/1998 | Sembert . |
| 5,723,063 | 3/1998 | Jie . |
| 5,807,299 | 9/1998 | McRoberts ................................ 602/67 |

*Primary Examiner*—Michael A. Brown

[57] ABSTRACT

The invention is directed to a cold compress especially adapted for applying cooling effect to the human genitalia. The invention includes a holder that can fit around the waist of a human having a pouch for holding a cooling member. The cooling member can be easily inserted in and remove from the pouch, and a number of cooling members can be used, so that a constant cooling effect can be applied to the human genitalia for the purposes of relieving trauma.

7 Claims, 2 Drawing Sheets

COLD COMPRESS FOR HUMAN GENITALIA

BACKGROUND OF THE INVENTION

The invention is directed to a cold compress adapted for applying a cooling effect to the human genitalia. The invention has a structure that specifically conforms to shape of the human genitalia, so that a specific portion or portions of the human genitalia can be cooled. The invention is useful for reducing pain after an operation, increasing male fertility, and other uses.

DESCRIPTION OF THE PRIOR ART

The invention relates to therapeutic ice packs adapted for the reduction of swelling and the relief of pain resulting from soft tissue surgery or trauma. The invention is concerned with ice packs having a structure especial adapted for use with the human genitalia.

Ice packs and dressings and other cooling bandages have been widely used within the medical field for therapeutic treatment of swelling and for the reduction of pain resulting from traumatic injuries or surgery. The effect of reduction of temperature in an area of injury facilitates the reduction in extravasation of fluids from the intracellular compartment into the interstitial areas which causes swelling. Ice packs have proven to be convenient and effective in reducing swelling locally. The application of ice packs in a localized area reduces pressure at the injured site and thereby substantially reduces pain within the first six to twelve hours after injury or operation. Also, ice packs will aid in the constriction and the maintenance of capillary vessels to retard or cease bleeding resulting from severed vessels.

Ice packs are generally composed of flexible material containing a freezable medium therein. For example, U.S. Pat. No. 3,506,013 of Zdenek described a disposable sterile iced dressing having one or more storage compartments which, at the time of manufacture, are filled with a suitable liquid such as water, hermetically sealed, sterilized and packaged within a protective container. It is described that these bandages can be placed on a form shaped in accordance with a predetermined portion of a patient's body to which they are to be applied and while on said form frozen to provide a preshaped rigid sterile iced dressing.

U.S. Pat. No. 4,092,982 of Salem described a therapeutic wrap comprising an outer strip being of an elongated, resilient elastic bandage and an inner strip of flexible material formed into a pocket or pockets having a partially secured overlapping flap, the pocket or pockets containing prepackaged cooling materials. The inner and outer strips are attached to one end and are secured to each other along their length by at least one loop attached to the strip of pockets and encircling the resilient bandage, whereby the loop do not inhibit the resilient movement of the outer strip.

In U.S. Pat. No. 4,596,250 of Beisang, III, et al., a movable cooling/heating device with directional of cooling/heating is described. The device contains a mixture of deionized water, propylene glycol, polysaccharides and plant gum for providing a moldable pillow-like surface for cooling/heating and positioning body organs or parts. The inclusion of appropriate phase change chemicals or reciprocal ion-type chemicals or metals particles facilitate the stabilization of temperature over a predetermined temperature range. Another composition for use in preparation of cold packs is described in U.S. Pat. No. 5,723,063 of Jie. This composition is comprised 7–85% water, 4–10% salt, 8–15% glycerin and 2–6% polyacrylamide.

The aforesaid ice packs have a major disadvantage in that they do not have a structure especially adapted for use with the human genitalia. Further, these packs have integrally formed structures where the cooling medium is formed together with the remaining bandage and structure for attaching the bandage to the human body part. Thus, once the cooling effect of the cooling medium has dissipated, a completely new bandage must be applied.

Athletic supporters are known in the art, such as those described in U.S. Pat. Nos. 3,782,375 of Donars and 4,679,554 of Markham. These devices while having a structure for fitting human male genitalia, provides no means for cooling the genitalia. Accordingly, they are deficient in that they cannot provide any pain relief by cooling the human genitalia.

U.S. Pat. No. 4,253,464 of Zorgniotti et al. described a method and device for contributing to the ovulating of male fertility including the use of providing a cooling surface in a position adjacent to and surrounding about the peripheral of the testis connected to a source of evaporated fluid for reducing testicular temperature. This device is bulky and impractical in use. U.S. Pat. No. 5,716,319 of Sembert described a method of delaying ejaculation during sexual intercourse where a pouch adapted for receiving and holding the testicles including a compress cools the testicles to delay ejaculation of the male during intercourse. The pouch described in this patent is only used for a single application and has a structure that is uncomfortable during use. Also, the cold compress as described therein is only applied to the back side of the testicles.

In summary, the dressings proposed in the prior art are deficient for a number reasons. Firstly, they do not have a shape conforming to the shape of the human genitalia, and thus are not effective for cooling the same. Secondly, they do not provide a system or means for replacing or replenishing the cooling effect, once the cooling medium has lost its cooling ability, without completely replacing the entire dressing.

SUMMARY OF THE INVENTION

The present invention avoids the aforesaid disadvantages of the prior art. The invention provides for the application of a cooling member containing, for example, crushed ice or soft ice mixture, to a specific location of the human genitalia. In the invention the location of the cooling member can be adjusted to a specific location of the human genitalia. In the invention the cooling member is held in placed by device containing a pouch so that the cooling member can be quickly and easily inserted and removed from the pouch. After a first cooling member has lost its cooling effect, it can be removed from the pouch, and another fresh cooling member can be inserted therein. This procedure can be repeated to continuously apply a cooling effect to the specific location of the human genitalia.

DESCRIPTION OF THE PREFERRED EMBODIMENTS

The invention is especially adapted to provide relief from pain after surgical procedures are perform on the human genitalia, such as a vasectomy or after the human genitalia has been traumatized. Before the vasectomy, the doctor may give the patient a mild sedative to relax him. When the local anesthetic is injected into the skin of the scrotum, there is some discomfort. But as soon as it takes effect, the patient should feel no pain. The vasectomy can then proceed without pain. A typical vasectomy includes making two small incisions, usually in the upper area of the scrotum. Through these incisions two tiny tubes (the vas deferens) are cut, and cauterized. The incisions are then closed with sutures.

Afterwards, the patient will be sore for a couple of days. The present invention is designed to reduce this soreness or pain. The invention by applying a cold compress to the area of the incisions reduces the soreness and pain and also reduces inflammation. The present invention is useful to repeated apply a cooling member having a cold temperature storage medium therein to the area of the incision, thereby providing constant cooling relief from pain over a long period of time, such as 48 to 72 hours after a vasectomy. Since the invention can provide a cooling affect to the male genitalia over a long period of time, it can effectively produce an intrascrotal temperature reduction for improving semen quality, along the lines as described in U.S. Pat. No. 4,253,464 of Zorgniotti et al.

The structure of the holding member according to the present invention can be similar to that of an athletic supporter or human underpants with a pouch covering the genitals, the pouch containing a removable ice pack or equivalent cooling member that contains ice or other cold temperature storage medium. This arrangement provides effective relief by cooling the male genital area, thereby reducing and decreasing the need for pain medication. Further, the support provided by the elastic material surrounding the male genitals and the ice pack will add to the control of discomfort by maintaining constant cooled pressure against the male testicles while holding the male testicles in place.

Figure 1:
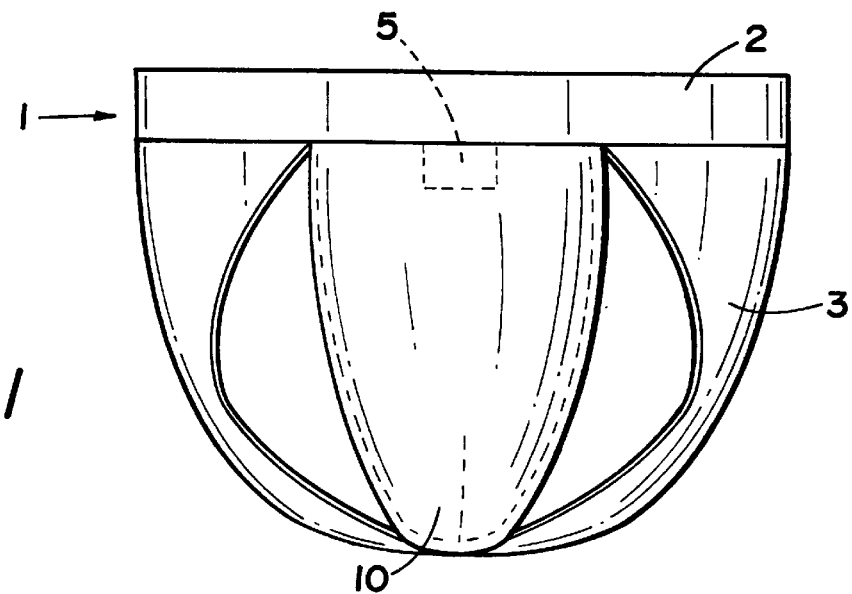
FIG. 1 is a frontal view of the compress according to the present invention.
Figure 2:
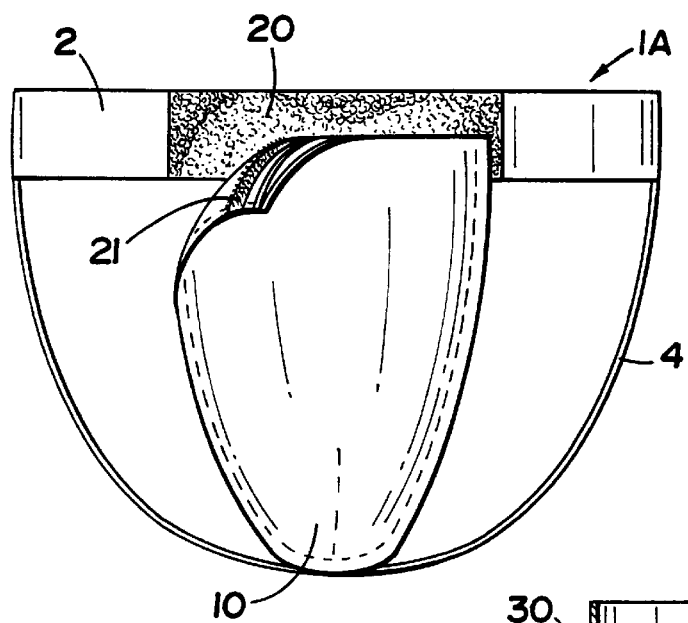
FIG. 2 is a frontal view of the holding member in accordance with the present invention, which utilizes hook and loop fasteners for securing the pouch to the waistband of the holding member.
Figure 3:
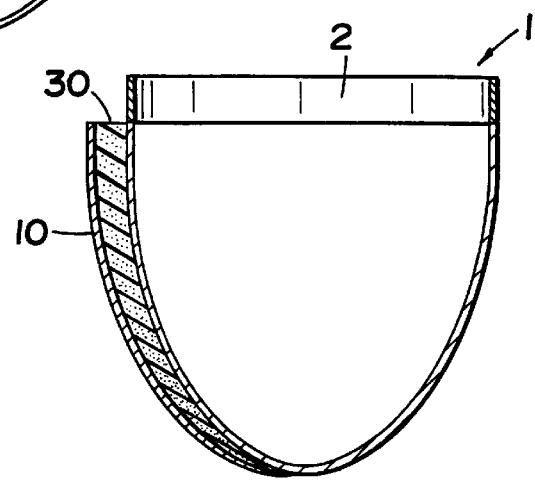
FIG. 3 is a cross-sectional view of the present invention.

The holding member can have a structure such as shown in FIGS. 1 and 2. The holders 1 and 1A in FIGS. 1 and 2 include a waistband 2, side panels 3 or side straps 4, and a pouch 10. Contained within the pouch is a cooling member 30 as shown in FIG. 3. The materials making up the waistband 2, side panels 3, straps 4, pouch 10, etc., for the holding member of the present invention can be the same as those used for athletic supporters and human undergarments in the prior art. See for example, U.S. Pat. No. 4,679,554 of Markham and U.S. Pat. No. 5,003,972 of Kestler, both of which are incorporated herein by reference. The pouch 10 can be stitched to the waistband as shown in FIG. 1. Alternatively, the pouch 10 can be secured to the waistband by the use of hook and loop fasteners. See, for example, FIG. 2 where a material having a plurality of loops 20 is provided on the waistband 2 and a material having a plurality of hooks 21 is provided on the upper end of the pouch 10 or vice versa. In this manner, the location of the pouch as well as the cooling member 30 contained therein can be adjusted so that the cooling effect of the cooling member is provided at a desired location of the genitalia.

Figure 7:
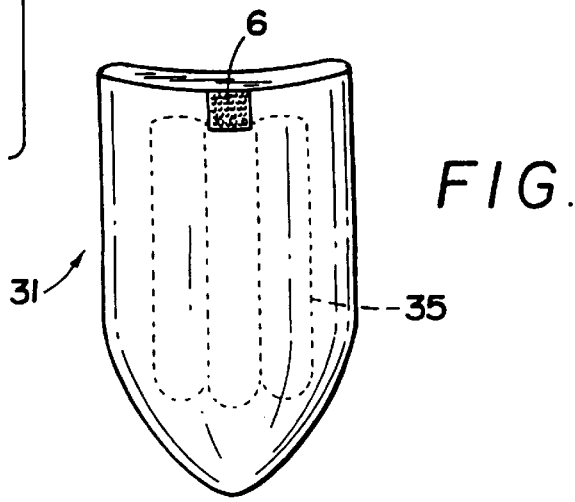

The hook and loop fasteners 20, 21 in FIG. 1 show a means of adjustably attaching the pouch to the waistband. The hook and loop fasteners can consist of a strip of nylon with a surface of minute hooks that fasten to a corresponding nylon strip with a surface of uncut pile, such as Velcro®. Other fastening means can be used, such as a plurality of snaps a plurality of buttons and button holes, a plurality of hooks with eyes, etc. The cooling member 30 can be secured in the pouch by fixing means, such as by hook and loop fasteners, where one of the hook and loop fasteners is provided in the pouch, such as shown at 5 in FIG. 1, and the other of the hook and loop fastener 6 is provided on the cooling member 31 as shown in FIG. 7.

Figure 4:
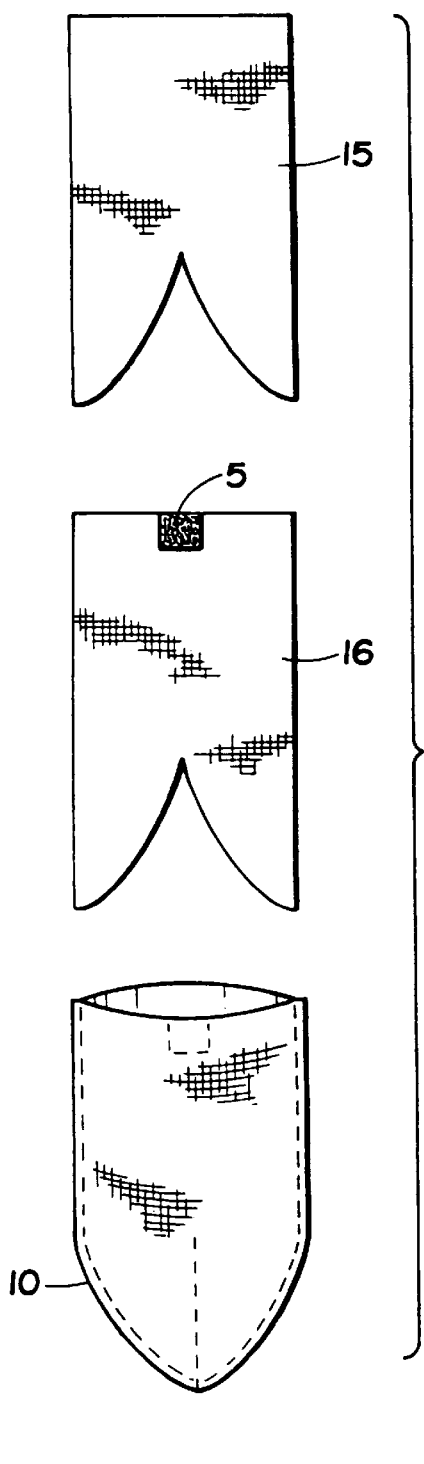
FIG. 4 shows formation of the pouch in the present invention.

FIG. 4 shows a construction for the pouch, including an outer elastic material 15 and an inner elastic material 16, the latter of which may have one of the hook and loop fastener 5 thereon. These materials are sewn together as shown at the bottom of FIG. 4 to form the pouch 10. Other structure for the pouch are also usable in the present invention, so long as the pouch can hold the cooling member in an appropriate location about the human genitalia.

The pouch of the holding member could be replaced with or have the structure of a backing material having strips sewn therein with Velcro strips on one end thereof, such as shown in U.S. Pat. No. 3,782,375 of Donars, which is incorporated herein by reference, where corresponding strips of Velcro could be provided on the cooling member 30, such as shown in FIG. 6.

The cooling member can have structure such as shown in FIGS. 3, 5, 6 and 7. In FIG. 3 the cooling member 30 is made from a flexible material such as sponge rubber that can be immersed in water so that water is absorbed therein, and then the sponge rubber is placed in a freezer for freezing the absorbed water. The sponge rubber can have a preformed shape conforming to the shape of the human genitalia. A sealable cover can be provided for the sponge rubber, so that when the ice melts, it is contained within the cover. For example, sponge fingers can be shaped to fit within the tubes 36 shown in FIG. 5, saturated with water, placed within in the tubes of FIG. 5, and the cooling member sealed with cover 34. Alternatively, the cooling member can have a flexible hollow structure of a unitary structure where a skin of rubber-like material completely encapsulates a cold temperature storage medium (i.e., water) therein. The skin can be made of a flexible material such as polyethylene, rubber, plastic or other synthetic and natural materials.

It is important that the cooling member and pouch holding the cooling member have a shape matching that of the human genitalia. This structure assists in applying the cooling action of the cold temperature storage medium of the cooling member to the traumatized portion of the human genitalia. In addition to the structures shown in the drawings, the holding member and cooling member can have a structure matching that of the female genitalia. For example, the invention can have a shape complimentary to the rectal-vaginal region of female humans, and thus could be used to relieve pain and reduce swelling for females after soft tissue surgery or trauma.

Figure 5:
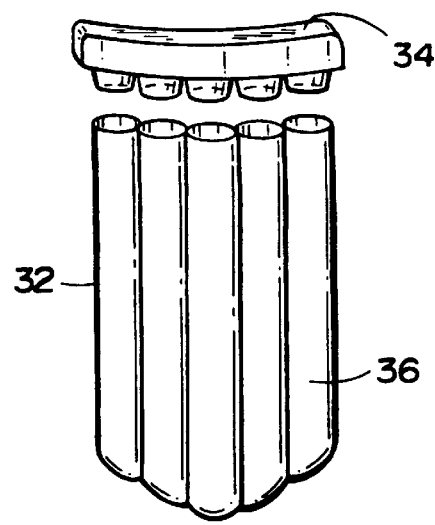
FIGS. 5 through 7 show various cooling members in accordance with the present invention.
Figure 6:
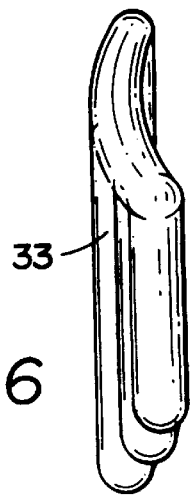

As shown in FIGS. 5 and 6, the cooling medium can be formed from a plurality of tubes 36 that extend in a parallel relationship. The use of the tubes assists in maintaining the cooling medium along the length of the cooling medium and prevents the cold temperature storage medium from collecting at the bottom of the cooling member. If the cold temperature storage medium collects in the bottom of the cooling medium, the cooling effect applied to the upper area of the scrotum, such as where a vasectomy was performed, is insufficient.

The plurality of tubes shown in FIGS. 5 and 6 can be made from any water impermeable substance, such as rubbers and plastics including those materials described above for the skin of cooling member having a flexible hollow structure. Any cold temperature storage medium can be contained in the tubes. The cold temperature storage medium can be water, closed cell foams of polymer materials, such as those described in U.S. Pat. No. 4,534,354 of Bonner, Jr. et al., and U.S. Pat. No. 4,556,055 of Bonner, Jr., both of which are incorporated herein by reference. Aqueous and nonaqueous mixtures can also be used as the cold temperature storage medium, such as within the plurality of tubes, including phase change materials of lithium chlorate, tetradecane, decanol, any C-15 through C-16 parafin, tetrahydrofuran and trimethylamine, along the line of those described in U.S. Pat. No. 4,596,250 of Beisang, III, et al., which is incorporated herein by reference. Other mixtures that can be used as the cold temperature storage medium include aqueous compositions containing glycerin and polyacrylamide, such as shown in U.S. Pat. No. 5,723,063 of Jie, which is incorporated herein by reference.

Further, the cooling member can have a structure such as shown at 31 in FIG. 7 where the dressing is provided with a plurality of separate storage compartments, which can be separated by stitching 35 or other means, and where a cold temperature storage medium is provided within the separated storage compartments. The resulting container can be formed to have a shape such as shown in FIG. 7 or other suitable shape for contacting the human genitalia.

FIG. 6 shows a cooling member where the tops of the tubes are sealed. In FIG. 5 the tops of the tubes are not sealed, but opened. The cap 34 corresponding to the openings of the tubes 36 is provided. With this arrangement crushed ice or another cold temperature storage medium can be inserted into the tubes, the cap 34 secured thereon to provide a water tight arrangement, and then the resulting cooling member 32 can be inserted into the pouch 10.

The use of sponge rubber or a cooling member such as shown in FIG. 5 permits the packaging of the cooling member together with the holding member without water or other cold temperature storage medium contained therein. In this way the invention can be packaged in a light weight and compact manner that can easily be given to patients in need of the same. Thereafter, the patient after returning home from the hospital or outpatient facility can add water or other cold temperature storage medium to the cooling medium, such as in the tubes 36 of the cooling medium shown in FIG. 5, and freeze and use the same.

An advantage of the present invention is that a plurality of any of the cooling members 30–33 can be frozen in advance or an individual cooling member, such as the cooling member 32, can be repeatedly used in the pouch, removed and refrozen, and then replaced in the pouch, so that a constant cooling is provided to the human genitalia area. The pouch 10 provides a structure permitting easy and quick access for inserting and removing cooling members 30–33 without discomfort to the patient, so that constant cooling can be applied to the human genitalia.

We claim:

1. A compress comprising a removable cooling member and a holding member, the holding member having a shape matching that of human genitalia for holding the removable cooling member at a specific location of human genitalia and having a pouch for receiving the removable cooling member, a waistband and straps, the pouch having a top and a bottom, the straps respectively having one end secured to the bottom of the pouch and another end secured to the waistband, the top of the pouch being secured to the waistband, and the removable cooling member including a cold temperature storage medium for cooling the specific location of human genitalia, wherein the cooling member has a plurality of tubes holding the cold temperature storage medium.

2. The compress according to claim 1, wherein the tubes have closed ends and the cold temperature storage medium is moldable when cold so that it can be fitted about a scrotum.

3. The compress according to claim 1, wherein the tubes have a closed bottom and an opened top, the cooling member further comprises a cap for closing the opened top of the tubes, and the cold temperature storage medium is crushed ice placed inside the tubes.

4. The compress according to claim 1, wherein the pouch includes inner and outer layers of fabric, the inner and outer layers of fabric are secured together at respective edges thereof and form a chamber for holding the cooling member.

5. The compress according to claim 1, wherein holding member includes means for securing the cooling member within the pouch.

6. The compress according to claim 1, wherein the pouch is adjustably secured to the waistband.

7. The compress according to claim 1, including a plurality of cooling members.

* * * * *